United States Patent [19]

Sassi et al.

[11] Patent Number: 5,631,337
[45] Date of Patent: May 20, 1997

[54] THERMOREVERSIBLE HYDROGELS COMPRISING LINEAR COPOLYMERS AND THEIR USE IN ELECTROPHORESIS

[75] Inventors: Alexander P. Sassi, Berkeley; Shi Lin, Fremont; M. Goretty Alonso-Amigo, Santa Clara; Herbert H. Hooper, Belmont, all of Calif.

[73] Assignee: Soane BioScience, Hayward, Calif.

[21] Appl. No.: 589,026

[22] Filed: Jan. 19, 1996

[51] Int. Cl.$^6$ ................... C08F 220/56; C08F 222/38
[52] U.S. Cl. ................... 526/307.2; 526/306; 526/307.3; 526/310
[58] Field of Search ................... 526/306, 307.2, 526/307.3, 310

[56] References Cited

U.S. PATENT DOCUMENTS

| | | | |
|---|---|---|---|
| 3,452,182 | 6/1969 | Haas | 430/286.1 |
| 3,762,927 | 10/1973 | Haas | 526/315 |
| 4,035,319 | 7/1977 | Haas | 526/396 |
| 5,120,809 | 6/1992 | Lupo et al. | 526/306 |
| 5,274,167 | 12/1993 | Lange et al. | 526/306 |

OTHER PUBLICATIONS

Haas and Schuler, "Thermally Reversible Homopolymer Gel Systems," Polymer Letters (1964), 2:1095–1096.
Haas et al., "Synthetic Thermally Reversible Gel Systems. II," J. of Polymer Sci. (1967), 5:915–927.
Haas et al., "Synthetic Thermally Reversible Gel Systems. III," J. of Polymer Sci. (1970), 8:1131–1145.
Haas et al., "Synthetic Thermally Reversible Gel Systems. IV," J. of Polymer Sci. (1970), 8:1213–1226.
Haas et al., "Synthetic Thermally Reversible Gel Systems. V," J. of Polymer Sci. (1970), 8:1725–1730.
Haas et al., "Synthetic Thermally Reversible Gel Systems. VI," J. of Polymer Sci. (1970), 8:3105–3115.
Haas et al., "Synthetic Thermally Reversible Gel Systems. VII," J. of Polymer Sci. (1971), 9:959–973.
Yoshioka et al., "A Synthetic Hydrogel with Thermoreversible Gelation. I. Preparation and Rheological Properties," J.M.S. –Pure Appl. Chem. (1994), 113–120.
Righetti and Snyder, "Thermally Reversible Gels in Electrophoresis. I: Matrix Characterization," Applied and Theoretical Electrophoresis (1988), 1:53–58.

Primary Examiner—Tae Yoon
Attorney, Agent, or Firm—Flehr Hohbach Test Albritton & Herbert LLP

[57] ABSTRACT

Thermoreversible hydrogels comprsing non-ionic, linear copolymers, and methods of their use in electrophoresis, are provided. The subject copolymers comprise polyacrylamide backbones, where a portion of the acrylamide monomeric units compose hydrogen bonding groups as N-substituents. Combination of the subject copolymers with an aqueous phase provides thermoreversible hydrodgels which find use as separation media in electrophoretic applications.

18 Claims, No Drawings

THERMOREVERSIBLE HYDROGELS COMPRISING LINEAR COPOLYMERS AND THEIR USE IN ELECTROPHORESIS

INTRODUCTION

1. Field of the Invention

The field of this invention is electrophoretic separation media.

2. Background

Electrophoresis has become an increasingly indispensable tool in biotechnology and related fields. The ability to separate molecules by means of size, shape and charge has added numerous opportunities to identify specific compounds, determine purity, and allow for isolation of a compound in a relatively pure form. A variety of analytical techniques are predicated on the use of electrophoresis for the separation and analysis of the various components of interest that may be present in a particular sample. For example, electrophoresis may be used to identify a compound, where the components of a complex mixture are first separated and then subsequently identified by using markers such as antibodies, DNA probes or the like. Electrophoresis may also be used in the determination of the molecular weights of components in a sample.

Electrophoresis is usually performed in a separation media which provides for separation of the sample components as they migrate through the gel under the influence of an applied electric field. Generally, separation media which have found use in electrophoresis comprise a network of either linear or cross-linked polymers. Although a variety of different cross-linked and linear polymers have been studied for their suitability in electrophoretic applications, the most commonly employed polymers are agarose and cross-linked polyacrylamide.

Agarose gels, which comprise a linear alternating co-polymer of β-D-galactose and 3,6-anhydro-α-L-galactose in an electrophoresis buffer, have many advantages in electrophoresis. Because they are thermoreversible, i.e. they undergo a transition from a first flowable state to a second gel state in response to a change in temperature, agarose gels are easy to prepare. Furthermore, agarose gels have high mechanical strength, providing for ease of manipulation. Another advantage of agarose gels is their ability to separate large molecules, e.g. DNA from 200 bp to about 50 kbp. Despite these advantages, there are disadvantages to the use of agarose gels as an electrophoretic separation medium. One disadvantage of agarose gels is their inability to provide for adequate resolution of smaller sized components. Other disadvantages of agarose gels include the presence of gel impurities that can result in sample contamination, distortions due to electroosmotic flow, and the like.

Crosslinked polyacrylamide gels, which are prepared through polymerization of acrylamide monomer with a cross-linker, provide alternative separation media that overcome some of the problems associated with agarose. Polyacrylamide gels provide for high resolution of small sized sample components, e.g. they are capable of providing high resolution of DNA ranging in size from 6 to 1000 bp in length. Other advantages of cross-linked polyacrylamide gels are that: (1) they are optically transparent, providing for easy identification of separated sample components, (2) they do not bind charged analytes and do not engender electroosmotic flow, and (3) sample components recovered from the gels are extremely pure, as the gels do not contain contaminants, as are found in agarose gels. Unfortunately, since cross-linked polyacrylamide gels must be prepared in situ, their preparation is complicated and poses health risks, as the acrylamide monomers are toxic.

Because of the limitations of the currently employed electrophoretic separation media, for many electrophoretic applications it would be desirable to have a gel which combined the high resolving power, as well as other advantages, of cross-linked polyacrylamide with the thermoreversible nature of agarose.

Relevant Literature

Haas et al., J. Polym. Sci. B. (1964) 2: 1095, reports that poly(N-acrylylglycinamides) form thermoreversible gels in which the transition temperature of the gel rises with increasing concentration and molecular weight of the homopolymer. The copolymerization of N-acrylylglycinamide with acrylic acid, β-aminoethyl vinyl ether, N-methacrylylvaline and isopropylacrylamide was studied in Haas et al., J. Polym. Sci. A-2 (1967) 5:915 and Haas et al, J. Polym. Sci. A-1 (1970) 8:1131; 1213; 1725; and 3405. Haas et al., J. Polym. Sci. A-1 (1971) 9:959 reported that solutions of poly(N-methacrylylglycinamides) gel upon cooling. Yoshioka et al., J. M.S. Pure Appl. Chem. (1994) A31:113 reported the preparation of aqueous solutions of block copolymers of poly(N-isopropylacrylamide-co-n-butyl-methacrylate) and poly(ethylene glycol), exhibited reverse transition hydrogel behavior in that solutions gelled upon heating.

Acrylylglycinamide homopolymers and their copolymers with acrolein or methacrolein are reported in U.S. Pat. Nos. 3,452,182; 3,726,927 and 4,035,319.

SUMMARY OF THE INVENTION

Thermoreversible hydrogels comprising linear copolymers are provided. The subject copolymers comprise polyacrylamide backbones in which a portion of the acrylamide monomeric units comprise hydrogen bonding groups as N-substituents. By varying the nature of the copolymers, as well as the concentration of the copolymers in the aqueous phase in which they are present, thermoreversible hydrogels having a diverse range of physical characteristics are obtained. The subject thermoreversible hydrogels find use as separation media in electrophoretic applications.

DESCRIPTION OF TO THE SPECIFIC EMBODIMENTS

Thermoreversible hydrogels comprising copolymers are provided. The copolymers of the subject hydrogels are nonionic and comprise a linear polyacrylamide backbone in which a portion of the acrylamide monomeric units comprise hydrogen bonding groups as N-substituents. Upon combination of the subject copolymers with an aqueous phase, a thermoreversible hydrogel is produced that changes from a first, flowable state to a second, gel state over a narrow temperature range. The subject thermoreversible hydrogels find use as separation media in electrophoretic applications. In further describing the subject invention, the copolymers will be described first in greater detail followed by a description of thermoreversible gels comprising the subject copolymers, as well as their use in electrophoretic applications.

The copolymers of the subject invention are linear, nonionic copolymers comprising a polyacrylamide backbone, where a portion of the acrylamide monomeric units comprise N-substituent groups capable of hydrogen bonding.

The molecular weight of the subject polymers will be at least about 10 kD, more usually at least about 50 kD, and may be as high as 1000 kD or higher. The term acrylamide as used herein includes unsubstituted acrylamide and derivatives thereof, such as methacrylamide, and the like, as well as N-substituted derivatives thereof. The weight percent ratio of acrylamide monomeric units of the copolymer comprising N-substituent groups capable of hydrogen bonding will range from about 55:45 to 95:5, and will usually range from about 65:35 to 90:10.

The hydrogen bonding N-substituent groups of the copolymers will comprise a hydrogen bonding moiety bonded through a bond or linking group to the N atom of the acrylamide monomeric unit. The copolymers of the subject invention may be homogeneous as to the nature of the hydrogen bonding N-substituent group, or heterogeneous, comprising up to 6 different hydrogen bonding N-substituent groups, but will usually comprise no more than 4 hydrogen bonding N-substituent groups, more usually no more 2 hydrogen bonding N-substituent groups. The hydrogen bonding N-substituent group will be capable of forming inter- and intramolecular hydrogen bonds in an aqueous medium, and will comprise from 2 to 30 carbon atoms, usually from 2 to 20 carbon atoms, more usually from 2 to 10 carbon atoms, and may be aliphatic, alicyclic, aromatic or heterocyclic, particularly aliphatic or heterocyclic. The hydrogen bonding moiety of the group will generally be a carbamyl moiety. Particular substituent groups of interest include heterocyclic nitrogen bases, where the nitrogen is substantially neutral at neutral pH, amides, particularly aliphatic amides, and the like. Heterocyclic nitrogen bases of interest include: purines, such as guanine, adenine, hypoxanthine; pyrimidines, such as thymine, cytosine, inosine, uracil; as well as natural and synthetic mimetics thereof. Amides of interest will be α to the N of the acrylamide monomeric unit, and will include aliphatic amides, where the aliphatic portion of the aliphatic amide will range from 1 to 4 carbon atoms, usually 1 to 3 carbon atoms, more usually 1 to 2 carbon atoms.

The copolymers of the subject invention will be conveniently prepared from first and second monomers. First monomers that find use in the subject invention may be described by the formula:

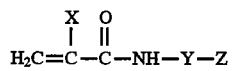

wherein:

X is H or $CH_3$,

Y is a bond or a linking group, where the linking group may be an aliphatic chain of from 1 to 6 carbon atoms, usually 1 to 4 carbon atoms, more usually 1 to 2 carbon atoms, where the aliphatic chain may be a straight or branched chain, comprising from 0 to 2 sites of unsaturation; and Z is a group comprising a hydrogen bonding moiety, where Z may be: from 2 to 30 carbon atoms, usually from 2 to 20 carbon atoms, more usually from 2 to 10 carbon atoms; will comprise from 2 to 10 heteroatoms, usually 2 to 8 heteroatoms, where at least one of the heteroatoms will be an N bonded to an H; and may be aliphatic, alicyclic, aromatic or heterocyclic, particularly aliphatic or heterocyclic, comprising 0 to 3 ring structures, usually 0 to 2 ring structures, where the ring structures may be fused and will generally be 5 to 6 atom rings.

The hydrogen bonding moiety present in the Z group will generally be a carbamyl group, where carbamyl group as used herein is described by the formula:

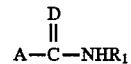

wherein:

A is C or a heteroatom;

D is O or S, usually O; and $R_1$ is H or an aliphatic substituent of up to 10 carbon atoms, usually up to 6 carbon atoms, more usually up to 4 carbon atoms, where the alkyl substituent may be straight or branched chain.

Where Z is an aliphatic amide, the first monomer will have the formula:

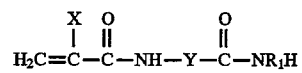

wherein:

X and Y and $R_1$ are the same as defined above;

Specific monomers that find use as first monomers in the subject invention include N-substituted acrylamide and the like. Preferably, the first monomer will be acrylylglycinamide. The subject monomers may be prepared according to known methods, such as those described in U.S. Pat. No. 3,452,182 for the preparation of amino substituted aliphatic amides, the disclosure of which is herein incorporated by reference.

The second monomer, which is copolymerized with the first monomer to produce the subject copolymers, will be acrylamide. Any N-substituents of the second monomer will not comprise a hydrogen bonding moiety. Preferably, the second monomer will be unsubstituted acrylamide.

The subject copolymers may be prepared according to known methods by combining the proper ratio of first and second monomers in a fluid phase and initiating polymerization. The ratio of first to second monomer which is combined in the aqueous phase will depend, in part, on the desired properties of the thermoreversible gel which is prepared from the copolymer, e.g. the desired melting temperature range at which a hydrogel comprising the copolymer will change from a gel to a flowable solution. Thus, if a hydrogel with a high melting temperature range is desired, the ratio of first to second monomers which are combined and co-polymerized will be high. Alternatively, the ratio of first to second monomers will be low if thermoreversible gels having a lower melting temperature range are desired. Generally, the mole ratio of first to second monomers will range from about 45:55 to 95:5, more usually from about 50:50 to 90:10.

The fluid phase employed for polymerization may be an aqueous or non-aqueous phase. A variety of aqueous phases may be employed, including pure water and water/lower alkanol mixtures, where the lower alkanol will typically be a C4 or smaller alkanol, such as ethanol, propanol, isopropyl alcohol and the like. Instead of, or in addition to, a lower alkanol, other polar organic solvents may be employed as co-solvents, such as dimethylformamide, dimethylsulfoxide and the like. The volume percent of the water in the aqueous phase will range from 10 to 100%. The volume percent of the co-solvent, when present, in the aqueous phase will not exceed 90%, and will usually not exceed 50%. A non-aqueous phase may also be employed, where the non-aqueous phase may be any convenient organic solvent, such as those listed above.

In some instances where the resultant copolymer and polymerization fluid phase are to be used directly as a separation media for electrophoresis, it may be convenient to include additional agents in the fluid phase which find use in electrophoresis. Additional agents of interest include various salts, particularly buffering salts, where the concentration of the buffering salts will vary from 0.01 to 0.5, more usually from 0.01 to 0.1M. The salts may include Tris, phosphate, EDTA, MOPS, and the like. Denaturing agents may also be present in the aqueous phase, particularly where the aqueous phase present during copolymerization will also serve as the continuous fluid phase in the hydrogel during electrophoresis. Denaturing agents that may be present in the aqueous phase include urea, SDS, formamide, methylmercuric hydroxide, alkali, and the like, where the concentration will vary depending on the particular denaturing agent, e.g. for urea, the concentration will range from about 0.1 to 9.0M.

Polymerization may be initiated using any convenient means, including both physical and chemical means. Physical means that may be employed include exposure to ultrasound, ultraviolet light and $\gamma$-ray irradiation. Chemical initiators that may be employed include: persulphate+3-dimethylaminopropionitrile (DMPAN), persulphate +tetramethylethylenediamine (TEMED), persulphate+heat, persulphate+thiosulfate, persulphate+bisulfite, persulphate+ diethylmethylaminediamine (DEMED), $H_2O_2+Fe^{2+}$, benzoyl peroxide, lauroyl peroxide, tetralin peroxide, actyl peroxide, caproyl peroxide, t-butyl hydroperoxide, t-butyl perbenzoate, t-butyl diperphthalate, cumene hydroperoxide, 2-butanone peroxide, azoinitiators, e.g. azodiisobutylnitrile and azodicarbonamide, riboflavin+visible light, methylene blue+a redox couple, and the like. Preferably a chemical polymerization initiator such as persulphate will be employed. When necessary to limit exposure of the monomers to oxygen during polymerization, polymerization may be carried out in an oxygen free atmosphere, such a nitrogen atmosphere.

Following polymerization, the resultant copolymers in combination with a fluid phase can be used directly as a separation medium for electrophoresis, where the concentration of the copolymers in the fluid phase provides for a hydrogel having properties suitable for use in electrophoresis, or the copolymers can be separated from the fluid phase and stored until later use, as appropriate. The copolymers can be recovered from the fluid phase using any convenient means, such as freeze drying or precipitation.

To prepare thermoreversible hydrogels from the subject copolymers, a sufficient amount of copolymer will be combined with an aqueous medium, where the aqueous medium provides the continuous fluid phase of the hydrogel. Generally, the amount of copolymer that is combined with the aqueous medium will range from about 1 to 30% T, and will usually range from about 2 to 20% T, more usually from about 3 to 15% T, where % T refers to the total weight of copolymer in grams per 100 ml of aqueous medium. As described above, the aqueous medium may comprise various agents that find use in electrophoresis, such as buffering salts, denaturing agents, and the like.

The subject thermoreversible hydrogels are characterized by undergoing a substantial physical change over a narrow melting temperature range ($T_m$), where below the $T_m$ the hydrogel is present as a gel like composition having a high viscosity and capable of electrophoretic sieving. Above the $T_m$ of the hydrogel, the hydrogel is present as a flowable, pourable composition having a low viscosity and being incapable of electrophoretic sieving. The $T_m$ of a particular hydrogel according to the subject invention, as well as the physical properties of the hydrogel above and below the $T_m$, will depend on the both the nature of the particular copolymer from which the gel is prepared, as well as the concentration of the copolymer in the aqueous phase. Generally, the subject hydrogels will have a $T_m$ between about 5° and 80° C., usually between about 10° and 70° C., and more usually between about 15° and 65° C. The magnitude of the narrow range of the $T_m$ will range from about 0.1° to 10° C., and will usually range from about 0.1° to 7.5° C., more usually from about 0.1 to 5.0° C. Above the $T_m$, the subject hydrogels will have a viscosity ranging from about 5 to 30,000 cps, more usually from about 20 to 10,000 cps, while below the $T_m$ the subject hydrogels will have a substantially infinite viscosity.

In addition to the subject copolymers described above, the thermoreversible hydrogels may further comprise one or more additional, non-proteinaceous, polymers that serve to modulate the physical and/or sieving characteristics of the hydrogel. These additional polymers may be linear or branched, and include hydroxyethylcellulose, hydroxypropyl cellulose, methyl cellulose, hydroxypropyl methyl cellulose, polyethylene glycol, polyethylene oxide, galactomannan, pullulan, dextran, polyvinyl alcohol, agarose, polyacryloylamino-ethoxyethanol and the like. The weight percentage of these additional polymers present in the hydrogel per milliliter of aqueous phase will depend on the particular additional polymer, the copolymer and the desired characteristics of the hydrogel. Generally, the T of the additional polymer or polymers in the hydrogel will range from 0.1 to 5.0%, more usually from 0.1 to 2.0%.

The subject thermoreversible hydrogels find use as separation media for electrophoretic applications. Electrophoretic applications in which the subject hydrogels find use as separation media are well known, being described in Andrews, Electrophoresis (1986) and Barron & Blanch, Separation and Purification Methods (1995) 24:1–118, and need not be reviewed in great detail here. Briefly, in electrophoretic applications, the subject media will be placed in an electrophoretic separation chamber, e.g. a slab gel container, column, channel, capillary and the like, of an electrophoretic device. Although the electrophoresis device can be prepared by producing the thermoreversible hydrogel in situ, typically a pre-prepared hydrogel will be introduced into the electrophoretic chamber, where the hydrogel is in the first, flowable state. Thus, the hydrogel may be prepared as described above and then introduced into the separation chamber of the electrophoretic device when the temperature of the hydrogel is above the $T_m$, i.e. as a pregel solution. After being introduced into the separation chamber, the temperature of the hydrogel may then be lowered so that the hydrogel assumes a gel state, capable of electrophoretic sieving. The hydrogel may be introduced into the separation chamber using any convenient means. Thus, for slab gel holders, it may be sufficient to simply pour the pregel solution into the slab gel holder while the hydrogel is above the $T_m$. Alternatively, for capillary holders, it may be more convenient to introduce the gel, while in a fluid state, into the interior volume of the capillary through injection or suction.

Once the hydrogel has been introduced into the separation chamber of the electrophoretic device and the temperature of the hydrogel reduced to below the $T_m$, a sample may be introduced into the hydrogel for electrophoresis. Where convenient, the hydrogel may be pre-electrophoresed, where pre-electrophoresis can serve a variety of purposes, such as for introduction of separation buffer, and the like. Sample components which may be separated in the subject hydrogels include nucleic acids, proteins, carbohydrates and the like. The sample may be introduced into the gel using a variety of methods, with the particular method selected dependent on the type of device being employed. Electrophoresis of the sample in the hydrogel may then be carried out in accordance with known procedures.

Following electrophoresis, the separated sample components may be analyzed in the gel, e.g. by staining and the like. The electrophoretically separated sample components may be removed from the gel for further analysis. Depending on the particular electrophoretic device being employed, separation may be accomplished by blotting, or by raising the temperature of the hydrogel above the $T_m$ and then extracting the sample component of the interest from the resultant fluid medium.

In addition to their use in electrophoresis, the subject copolymers find use in other separation applications such as chromatography, as well as in membranes, controlled release compositions, contact lenses, and the like.

The following examples are offered by way of illustration and not by way of limitation.

EXPERIMENTAL

A number of different copolymers of acrylylglycinamide and acrylamide were prepared and their characteristics were compared to homopolymers of polyacrylylglycinamide.

A. Gels of Acrylylglycinamide and Acrylamide Copolymers (AGA)

1. T8% Copolymer AGA50

A copolymer of acrylylglycinamide (AG) and acrylamide (AA) was prepared by combining AG and AA monomers in pure water at room temperature with ammonium persulphate (APS) and N,N,N'N'-tetramethylethylenediamine (TEMED) as polymerization initiators. The weight percent ratio of AG to AA monomers was 50:50. The concentration of total monomer prior to polymerization was 8%. Upon polymerization at room temperature, a solution of a linear viscous polymer was obtained.

2 T7.3% Copolymer AGA 73

The procedure used to produce the T8 AGA50 was employed, except that the ratio weight percent of AG to AA was changed to 73:27, and the concentration of total monomer prior to polymerization was 7.3%. Following polymerization at room temperature a thermoreversible clear gel was obtained. The resultant hydrogel had a $T_m$ of 36.5° C.

3. T6.4% Copolymer AGA90

The same procedure as used to prepare the T7.3% AGA73 gel was employed, except that the weight % ratio of AG to AA was changed to 90:10 and the concentration of total monomer prior to polymerization was 6.4%. Polymerization yielded a transparent gel at room temperature which had a $T_m$ of 63.9° C. The resultant T6.4% AGA90 gel was observed to be mechanically stronger and more stable than the T7.3% AGA73 gel.

4. T7% AGA72 Gel

The same procedure used to prepare the above hydrogel compositions of examples 1–3 was employed, except that the weight % ratio of AG to AA was changed to 72:28, and the concentration of total monomer prior to polymerization was 7%. Following polymerization, a clear gel was obtained.

To study the suitability of the resultant hydrogel as a separation medium for electrophoresis, 0.5 ml of 10×TBE buffer and 0.1 μl of ethidium bromide were added to 10 ml of the hydrogel pregel solution solution at 80° C., to achieve a final TBE concentration of 0.5×. The resultant hydrogel was cooled in a refrigerator prior to use in electrophoresis. Separation of a 100 bp ladder and ΦX174/Hae III was carried out at 12 V/cm. The gel separated 7 bands of a possible 15 bands of the 100 bp ladder and 6 bands of a possible 11 bands of the ΦX174/Hae III.

5. T5.3% AGA89

The same procedure used to prepare the above hydrogel compositions of 1–4 was employed, except that the weight % ratio of AG to AA was changed to 89:11, and the concentration of total monomer prior to polymerization was 5.3%. Following polymerization, a hydrogel having a $T_m$ of 57° C. was obtained which was stronger than the T7% AGA90 hydrogel.

The separation capability of the resultant hydrogel was studied using the same procedure as that used in 4, above. The T5.3% AGA89 gel provided better separation of dsDNA than did the T7% AGA90 hydrogel described in 4, above.

6. T2.8% AGA 89.

Sufficient water was added to the T5.3% AGA89 hydrogel to reduce the AGA89 concentration from 5.3% to 2.8%. The resultant composition provided a clear gel at room temperature.

7. T5.3% AGA 89 7.1M Urea Gel

Sufficient urea was added to the composition of T5.3% AGA89 hydrogel at 85° C. to achieve a urea concentration in the gel of 7.1M. Upon cooling of the hydrogel to room temperature, a clear gel was obtained.

B. Gels of Polyacrylylglycinamide Homopolymers (PAG)

1. T5% Homopolymer PAG

10 μl TEMED, 20 μl 10% APS and sufficient AG were added to 10 ml pure water to achieve an AG monomer concentration of 5%. Following polymerization at room temperature, an opaque gel was obtained that became clear when the temperature of the gel was raised to 85° C. The resultant gel was not thermoreversible.

2. T5.5% PAG 0.5 g AG, 9g H$_2$O, 0.2 g isopropyl alcohol, 20 μl TEMED and 40 μl 10% APS were combined at room temperature. Following polymerization, a gel was obtained that was opaque at 25° C. and clear at 90° C. The resultant gel was not thermoreversible.

3. T5.3% PAG.

This gel was prepared in the manner as the gel in 2, except that polymerization was carried out 65° C. Upon polymerization, a reversible gel was obtained with a $T_m$ of 71° C.

C. Comparison of AGA Hydrogels to PAG Gels

In comparing the properties of the AGA hydrogels to the gels of PAG homopolymer, several differences become apparent. While gels of PAG polymerized in pure water have been reported to form insoluble, though water swellable gels, hydrogels of AGA in pure water were found to gel at room temperature and dissolve upon heating. Furthermore, while small quantities of hydrogen bond breaking reagents such as urea and thiocyanate have been reported to readily dissolve PAG gels, the T5.3% AGA89 gel was found to be stable at urea concentrations in excess of 7M. While the addition of water to PAG gels has been reported to dissolve the gels, it was found that addition of a significant amount of water to the T5.3% AGA89 gel did not dissolve the gel. Finally, while a 5.27% PAG gel has been reported to have a $T_m$ of 24° C., the $T_m$, of T5.3% AGA89 which has roughly the same concentration of polymer was found to be 57° C., which is significantly higher.

Hydrogels comprising the AGA copolymer were found to have much higher strength and elasticity than PAG homopolymer gels, making them comparatively easier to manipulate. Furthermore, hydrogels comprising the AGA copolymer are transparent and highly hydrophilic, and provide for excellent electrophoretic separation when the gels are employed as electrophoretic separation media.

From the above results and discussion, it is apparent that thermoreversible hydrogels particularly suited for use as separation media for electrophoresis are provided. The thermoreversible hydrogels are easy to prepare and use, are adaptable to a variety of electrophoretic devices, buffer and denaturing systems, are mechanically strong, are transparent for easy sample identification, and are capable of providing for high resolution of separated sample components.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A non-ionic, linear copolymer capable of forming a thermoreversible hydrogel when combined with an aqueous phase, said copolymer comprising:

a polyacrylamide backbone, wherein 55 to 95 weight percent ratio of the acrylamide monomeric units of said copolymer comprise N-substituent groups capable of hydrogen bonding.

2. The copolymer according to claim 1, wherein said copolymer has a molecular weight of about 10 kD to 1000 kD.

3. The copolymer according to claim 1, wherein said N-substituent groups capable of hydrogen bonding comprise a carbamyl group as a hydrogen bonding moiety.

4. The copolymer according to claim 1, wherein said hydrogen bonding group is a heterocyclic nitrogen base.

5. The copolymer according to claim 1, wherein said hydrogen bonding group is an α-aliphatic amide.

6. A non-ionic, linear copolymer capable of forming a thermoreversible hydrogel when combined with an aqueous phase, said copolymer comprising:

first and second monomeric units in a weight percent ratio of from about 55:45 to about 95:5, wherein said first monomeric unit is of the formula:

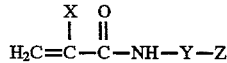

wherein:
X is H or CH$_3$,
Y is a bond or a linking group of from 1 to 6 carbon atoms; and
Z is a group comprising a hydrogen bonding moiety, wherein said hydrogen bonding moiety is of the formula:

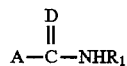

wherein:
A is C or a heteroatom;
D is O or S; and
R$_1$ is H or an aliphatic substituent of up to 10 carbon atoms; and
said second monomeric unit is acrylamide.

7. The copolymer according to claim 6, wherein Z is a heterocyclic nitrogen base selected from a purine or pyrimidine.

8. The copolymer according to claim 6, wherein Z is an α-aliphatic amide.

9. The copolymer according to claim 6, wherein said linking group is aliphatic chain of from 1 to 6 carbon atoms.

10. A copolymer of acrylylglycinamide and acrylamide, wherein the weight percent ratio of acrylylglycinamide to acrylamide of said copolymer ranges from about 55:45 to about 95:5.

11. A thermoreversible hydrogel suitable for use as a separation medium for electrophoresis, said hydrogel comprising:

a non-ionic, linear copolymer comprising a polyacrylamide backbone, wherein 55 to 95 weight percent ratio of the acrylamide monomeric units of said copolymer comprise N-substituent groups capable of hydrogen bonding; and a continuous fluid phase.

12. The thermoreversible hydrogel according to claim 11, wherein said thermoreversible hydrogel has a T$_m$ ranging from about 15° to 65° C.

13. The thermoreversible hydrogel according to claim 11, wherein the amount of said copolymer in said hydrogel ranges from about 1 to 30% T.

14. A thermoreversible hydrogel suitable for use as a separation medium for electrophoresis, said hydrogel comprising:

a non-ionic, linear copolymer comprising first and second monomeric units in a weight percent ratio of from about 55:45 to about 95:5, wherein said first monomeric unit is wherein said first monomeric unit is of the formula:

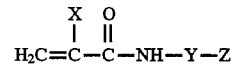

wherein:
X is H or CH$_3$,
Y is a bond or a linking group of from 1 to 6 carbon atoms; and
Z is a group comprising a hydrogen bonding moiety, wherein said hydrogen bonding moiety is of the formula:

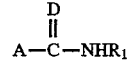

wherein:
A is C or a heteroatom;
D is O or S; and
R$_1$ is H or an aliphatic substituent of up to 10 carbon atoms; and
said second monomeric unit is acrylamide; and
a continuous liquid phase.

15. The thermoreversible hydrogel according to claim 14, wherein the amount of said copolymer in said hydrogel ranges from about 1 to 30% T.

16. The thermoreversible hydrogel according to claim 14, wherein said first monomeric unit is acrylylglycinamide.

17. A thermoreversible hydrogel suitable for use as a separation medium for electrophoresis, said hydrogel comprising:

a polyacrylamide backbone, wherein a portion of the acrylamide monomeric units of said copolymer comprise N-substituent groups capable of hydrogen bonding;

an additional, non-proteinaceous linear polymer; and
an aqueous phase.

18. The thermoreversible hydrogel according to claim 17, wherein said acrylamide monomeric units comprising N-substituent groups capable of hydrogen bonding are acrylylglycinamide.

* * * * *